(12) United States Patent
Tanaka et al.

(10) Patent No.: US 7,722,707 B2
(45) Date of Patent: May 25, 2010

(54) AIR CONDITIONER (75) Inventors: Toshio Tanaka, Osaka (JP); Kenkichi Kagawa, Osaka (JP); Kanji Motegi, Osaka (JP); Ryuji Akiyama, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 384 days.

(21) Appl. No.: 11/883,851

(22) PCT Filed: Feb. 20, 2006

(86) PCT No.: PCT/JP2006/302941

§ 371 (c)(1), (2), (4) Date: Aug. 7, 2007

(87) PCT Pub. No.: WO2006/090659

PCT Pub. Date: Aug. 31, 2006

(65) Prior Publication Data

US 2008/0120989 A1    May 29, 2008

(30) Foreign Application Priority Data

Feb. 25, 2005  (JP) .............................. 2005-052038

(51) Int. Cl.
*B03C 3/011* (2006.01)
*B03C 3/014* (2006.01)

(52) U.S. Cl. ...................... 96/57; 62/3.1; 95/69; 95/73; 96/58; 96/69; 96/74; 96/96; 422/186.04

(58) Field of Classification Search .................. 96/57, 96/58, 69, 74, 96–98; 95/67, 69, 70, 73; 62/3.1, 317; 422/186.04
See application file for complete search history.

(56) References Cited

U.S. PATENT DOCUMENTS

| 5,290,343 | A  | * | 3/1994  | Morita et al.      | 96/39  |
| 5,456,741 | A  | * | 10/1995 | Takahara et al.    | 96/22  |
| 5,476,539 | A  | * | 12/1995 | Suzuki et al.      | 96/44  |
| 6,092,387 | A  | * | 7/2000  | Hironaka et al.    | 62/317 |
| 6,164,082 | A  | * | 12/2000 | Okamoto et al.     | 62/317 |
| 6,193,782 | B1 | * | 2/2001  | Ray                | 95/4   |
| 6,224,653 | B1 | * | 5/2001  | Shvedchikov et al. | 95/58  |
| 6,251,170 | B1 | * | 6/2001  | Hironaka et al.    | 96/28  |
| 6,332,331 | B1 | * | 12/2001 | Cheng et al.       | 62/275 |
| 6,338,382 | B1 | * | 1/2002  | Takahashi et al.   | 165/96 |
| 6,436,170 | B1 | * | 8/2002  | McDermott et al.   | 95/58  |
| 6,517,608 | B2 | * | 2/2003  | McDermott et al.   | 95/58  |

(Continued)

FOREIGN PATENT DOCUMENTS

CN           2405398 Y       11/2000

(Continued)

*Primary Examiner*—Richard L Chiesa
(74) *Attorney, Agent, or Firm*—Birch, Stewart, Kolasch & Birch, LLP (57) ABSTRACT

A discharge unit (30) and a heat exchanger (20) are disposed in an air passageway (15). In the discharge unit (30), a rod-like discharge electrode (31) and a plate-like counter electrode (32) are disposed perpendicular to the flow of air, and lie along the heat exchanger (20). Upon application of voltage to both the electrodes (31, 32), streamer discharge is performed between the electrodes (31, 32), whereby an active species capable of decomposition of a component to be processed is produced.

10 Claims, 3 Drawing Sheets

U.S. PATENT DOCUMENTS

| | | | |
|---|---|---|---|
| 6,635,106 B2 * | 10/2003 | Katou et al. | 96/67 |
| 7,270,698 B2 * | 9/2007 | Tanaka et al. | 96/95 |
| 7,332,020 B2 * | 2/2008 | Tanaka et al. | 96/66 |
| 7,377,962 B2 * | 5/2008 | Tanaka et al. | 96/83 |
| 7,465,339 B2 * | 12/2008 | Tanaka et al. | 96/52 |
| 7,569,100 B2 * | 8/2009 | Tanaka et al. | 96/18 |
| 2006/0070526 A1 * | 4/2006 | Hong et al. | 96/69 |
| 2008/0314251 A1 * | 12/2008 | Tanaka et al. | 96/95 |
| 2009/0120781 A1 * | 5/2009 | Motegi et al. | 204/164 |
| 2009/0193976 A1 * | 8/2009 | Motegi et al. | 96/29 |
| 2009/0199718 A1 * | 8/2009 | Tanaka et al. | 96/54 |

FOREIGN PATENT DOCUMENTS

| | | | |
|---|---|---|---|
| CN | 1572329 A | | 2/2005 |
| JP | 63-297992 A | | 12/1988 |
| JP | 1-260230 A | * | 10/1989 |
| JP | 2002-346376 A | | 12/2002 |
| JP | 2003-65593 A | | 3/2003 |
| JP | 2005-21319 A | | 1/2005 |
| KR | 10-2004-0051029 A | | 6/2004 |

* cited by examiner

AIR CONDITIONER

This application is a national stage of PCT/JP2006/302941 filed on Feb. 20, 2006, which claims priority to Japanese Patent Application 2005-052038 filed on Feb. 25, 2005, the entire content of each of which is incorporated herein by reference.

TECHNICAL FIELD

The present invention relates generally to air conditioners for air conditioning of air to be treated, and is particularly concerned with air conditioners adapted and configured to effect purification of air to be treated.

BACKGROUND ART

Air conditioners for household use for providing air conditioning to indoor spaces have been known in the past. It is well known that many of such air conditioners have an air purifying function.

For example, JP-A-2003-65593 discloses a room air conditioner of the so-called "wall type" having an air purifying function. This air conditioner is provided, in its casing, with an air passageway through which air to be treated flows. In the air passageway are disposed a corona discharge part for decomposition of airborne odorous and harmful components (hereinafter referred to as the "component to be processed"), and a heat exchanger for conditioning of air. The corona discharge part includes a pair of electrodes and a power supply for application of pulse voltage of several KV to both the electrodes.

Upon introduction of air to be treated into the casing by operation of an air blower, the thus introduced air passes through the corona discharge part. In the corona discharge part, the voltage has been applied to both the electrodes and corona discharge is taking place between the electrodes. This consequently produces, in the corona discharge part, a radical or the like used for decomposition of the component to be processed present in the air, in other words the airborne component is decomposed by the radical. The thus purified air is conditioned in temperature to a predetermined level in the heat exchanger, thereafter being supplied through an outlet opening into an indoor space.

DISCLOSURE OF THE INVENTION

Problems which the Invention Seeks to Overcome

Incidentally, in order to save installation space or to enhance the aesthetic aspect of an indoor space, downsizing or low-profiling has been demanded for air conditioners of the indoor space installed type (e.g., wall-mounted type). On the other hand, air conditioners including a corona discharge part (e.g., the air conditioner disclosed in JP-A-2003-65593) require space to accommodate the corona discharge part, thereby resulting in increasing by that much the size/thickness of the apparatus.

With a view to seeking to overcome the problems with the prior art air conditioners, the present invention was devised. Accordingly, a general object of the present invention is to provide a compact air conditioner having an air purifying function.

Means for Overcoming the Problems

The present invention provides, as a first aspect, an air conditioner which includes an air passageway (15) through which air to be treated flows and an air conditioning means (20) for providing air conditioning to air flowing through the air passageway (15). The air conditioner of the first aspect is characterized in that the air passageway is provided with a discharge means (30) configured to perform streamer discharge.

In the first aspect of the present invention, the air conditioning means (20) and the discharge means (30) are disposed in the air passageway (15). During passage of the air to be treated through the air conditioning means (20), the air is conditioned in temperature and humidity. And, during passage of the air to be treated through the discharge means (30), a component to be processed present in the air is decomposed.

More specifically, in the discharge means (30) of the first aspect, streamer discharge is performed between a pair of electrodes. Upon occurrence of air dielectric breakdown caused by the streamer discharge, an active species (radical, fast electron, excited molecule et cetera) is generated. As compared to other types of discharges (e.g., corona discharge, glow discharge et cetera), streamer discharge is able to form a higher-density, wider active region for the active species. In other words, streamer discharge is able to generate active species of higher activity in larger amounts when compared to other types of discharges. Accordingly, it becomes possible to improve the efficiency of decomposition of the component to be processed per unit installation space.

The present invention provides, as a second aspect according to the first aspect, an air conditioner which is characterized in that the discharge means (30) comprises a discharge electrode (31) serving as a discharge base end and a counter electrode (32) serving as a discharge terminal end, and that the discharge electrode (31) is formed so as to extend, along the air conditioning means (20), in a direction perpendicular to the flow of air.

In the second aspect of the present invention, streamer discharge is generated to the counter electrode (32) from the discharge electrode (31). The discharge electrode (31) is formed so as to lie along the air conditioning means (20). This arrangement therefore makes it possible to accomplish compact housing of the discharge electrode (31) in the air passageway (15). In addition, the discharge electrode (31) is formed so as to extend in a direction perpendicular to the flow of air, whereby the air conditioner can be low-profiled in the direction of air flow.

The present invention provides, as a third aspect according to the second aspect, an air conditioner which is characterized in that the discharge electrode (31) is formed into a rod-like shape or into a linear shape and is disposed approximately in parallel with the counter electrode (32) which is shaped like a sheet.

In the third aspect of the present invention, the discharge electrode (31) is formed into a rod-like shape or into a linear shape. Consequently, in the discharge means (30), the tip of the discharge electrode (31) serves as a discharge base end and streamer discharge is generated therefrom towards the sheet-like counter electrode (32). As a result, the region of discharge from the tip of the discharge electrode (31) to the counter electrode (32) increases in electric field density, thereby making it possible to generate the aforesaid active species at high density.

In addition, approximately in a parallel relationship with the discharge electrode (31), the counter electrode (32) is disposed so as to be perpendicular to the flow of air. This arrangement therefore makes it possible to accomplish low-profiling of the air conditioner in the direction of air flow.

The present invention provides, as a fourth aspect according to the first aspect, an air conditioner which is characterized in that a catalytic means (40), adapted to be activated by an active species generated by streamer discharge from the discharge means (30) to thereby promote decomposition of a component to be processed, is disposed downstream of the discharge means (30).

In the fourth aspect of the present invention, the catalytic means (40) is disposed downstream, relative to the flow of air, of the discharge means (30). Consequently, the active species generated by the discharge means (30) flows through the catalytic means (40), along with air. As a result, the catalytic means (40) is activated, whereby the component to be processed is effectively decomposed.

The present invention provides, as a fifth aspect according to the fourth aspect, an air conditioner which is characterized in that the discharge means (30) and the catalytic means (40) are disposed upstream of the air conditioning means (20).

In the fifth aspect of the present invention, the air passageway (15) contains (in upstream to downstream order): the discharge means (30), the catalytic means (40), and the air conditioning means (20). In the first place, the air to be treated flows through the discharge means (30) and then through the catalytic means (40). During such passage, the component to be processed is decomposed by the aforesaid active species. In addition, the catalytic means (40) is activated, thereby promoting decomposition of the component to be processed. Thereafter, the air passes through the air conditioning means (20). In the air conditioning means (20), the air is conditioned in temperature or in humidity.

In the fifth aspect of the present invention, the air which has been conditioned in temperature or humidity by the air conditioning means (20) never flows through the catalytic means (40). Therefore, for example, adhesion of moisture present in the humidified air to the catalytic means (40) or vapor condensation of moisture present in the cooled air in the catalytic means (40) is avoided, thereby enabling the catalytic means (40) to satisfactorily exhibit its catalytic function.

The present invention provides, as a sixth aspect according to either the fourth or fifth aspect, an air conditioner which is characterized in that the catalytic means (40) supports thereon an adsorbent for adsorption of the component to be processed present in the air.

In the sixth aspect of the present invention, during passage of the air to be treated through the catalytic means (40), the component to be processed remaining in the air is adsorbed by the adsorbent.

The present invention provides, as a seventh aspect according to the first aspect, an air conditioner which is characterized in that the air passageway (15) is provided with a dust particle collecting means (41) for trapping dust particles present in the air. Here, by "dust particle collecting means" is meant a means including either a filter for trapping dust particles or an electrical dust collector for trapping electrically-charged dust particles by use of coulomb force.

In the seventh aspect of the present invention, during passage of the air to be treated through the dust particle collecting means (41), airborne dust particles are trapped by the duct particle collecting means (41). In other words, in the air conditioner of the seventh aspect, purification of the air to be treated by collecting airborne dust particles is accomplished, in addition to decomposition of the component to be processed.

The present invention provides, as an eighth aspect according to the seventh aspect, an air conditioner which is characterized in that the dust particle collecting means (41) is disposed upstream of the discharge means (30).

In the eighth aspect of the present invention, the dust particle collecting means (41) is disposed upstream, relative to the flow of air, of the discharge means (30). Accordingly, air after removal of dust particles therefrom flows into the discharge means (30). This therefore prevents adhesion of dust particles to the electrode of the discharge means (30).

The present invention provides, as a ninth aspect according to the second aspect, an air conditioner which is characterized in that the air conditioning means is formed by a conductive heat exchanger (20) which is disposed so as to face towards the discharge electrode (31), and that the heat exchanger (20) serves also as the counter electrode (32).

In the ninth aspect of the present invention, during passage of the air to be treated through the heat exchanger (20), heat exchange takes place between the refrigerant within the heat exchanger (20) and the air to be treated, whereby the air to be treated is conditioned in temperature. In the ninth aspect of the present invention, the heat exchanger (20) is disposed such that it faces towards the discharge electrode (31) and is utilized so as to serve also as the counter electrode (32). In other words, in the ninth aspect of the present invention, streamer discharge is generated towards the heat exchanger (20) from the discharge electrode (31), whereby the active species is generated in the air.

ADVANTAGEOUS EFFECTS OF THE INVENTION

In the first aspect of the present invention, it is arranged such that the discharge means (30) for generation of streamer discharge is disposed in the air passageway (15) of the air conditioner. As a result of such arrangement, in accordance with the first aspect of the present invention, it becomes possible to produce active species in larger amounts when compared, for example, to glow discharge and corona discharge, thereby enhancing the capability of decomposition of the component to be processed in the air conditioner. As a result, while achieving downsizing of the discharge means (30) and, furthermore, achieving downsizing/low-profiling of the air conditioner, it is possible to obtain stable air purification efficiency.

In accordance with the second aspect of the present invention, the discharge electrode (31) can be formed along the air conditioning means (20), thereby making it possible for the discharge electrode (31) and the air conditioning means (20) to be housed compactedly within the air conditioner. Especially, the discharge electrode (31) is disposed perpendicular to the flow of air, thereby making it possible to achieve low-profiling of the air conditioner in the direction of air flow.

In accordance with the third aspect of the present invention, it is arranged for streamer discharge to be generated from the tip of the rod-like discharge electrode (31) towards the counter electrode (32), as a result of which arrangement the discharge region is increased in electric field density, thereby making it possible to increase the amount of generation of the active species. Consequently, the capability of decomposing the component to be processed in the air conditioner is enhanced to a further extent and downsizing/low-profiling of the air conditioner is accomplished. In addition, the counter electrode (32) is also disposed perpendicular to the flow of air, thereby making it possible for the air conditioner to be further low-profiled in the direction of air flow.

Incidentally, if streamer discharge is generated from the tip of the discharge electrode (31) towards the counter electrode (32), this will cause the tip of the discharge electrode (31) to be gradually melted by heat accompanied with the streamer discharge. Stated another way, if in the discharge means (30) streamer discharge is generated over a long period of time, this causes the tip of the rod-like discharge electrode (31) to be gradually "withdrawn". Here, in the third aspect of the present invention, the discharge electrode (31) and the counter electrode (32) are disposed approximately in parallel with each other. Consequently, even where the tip of the discharge electrode (31) becomes "withdrawn", it is possible to maintain the distance between the discharge electrode (31) and the counter electrode (32) at constant interval. This therefore makes it possible for the discharge means (30) to continue to generate stable streamer discharge over a long period of time.

In accordance with the fourth aspect of the present invention, it is arranged such that activation of the catalytic means (40) is effected by the active species generated by the discharge means (30), as a result of which arrangement the capability of decomposing the component to be processed is further enhanced. Therefore, the discharge means (30) and the air conditioner can be further downsized.

In accordance with the fifth aspect of the present invention, it is arranged such that the catalytic means (40) is disposed upstream of the air conditioning means (20), as a result of which arrangement adhesion of moisture with respect to the catalytic means (40) is avoided. This therefore enables the catalytic means (40) to satisfactorily exhibit its catalytic function, whereby the capability of decomposing the component to be processed can be enhanced and, furthermore, the air conditioner can be downsized.

In accordance with the sixth aspect of the present invention, it is arranged such that the component to be processed remaining in the air is adsorbed by the adsorbent of the catalytic means (40). This arrangement ensues removal of the component to be processed, thereby making it possible to enhance the reliability of the air conditioner. In addition, in the sixth aspect of the present invention, the adsorbent is supported on the catalytic means (40). Accordingly, for example, when compared to the case where a different adsorbent from the absorbent supported on the catalytic means (40) is disposed in the air passageway (15), the air conditioner can be designed more compactedly.

In accordance with the seventh aspect of the present invention, it is arranged such that dust particles present in the air to be treated are trapped by the dust particle collecting means (41). This arrangement therefore makes it possible to simultaneously perform deodorizing and dust-colleting on the air to be treated, whereby the level of cleaning of the air to be treated is improved.

Especially, in the eighth aspect of the present invention, it is arranged such that the dust particle collecting means (41) is disposed upstream of the discharge means (30), as a result of which arrangement adhesion of dust particles with respect to the discharge means (30) is prevented. This therefore enables the discharge means (30) to generate stable streamer discharge over a long period of time.

Furthermore, by removal of airborne dust particles by the dust particle collecting means (41), dust particle adhesion with respect to the air conditioning means (20) is also prevented. Therefore, the air conditioning means (20) is prevented also from degradation in its air conditioning capability.

In accordance with the ninth aspect of the present invention, it is arranged such that the heat exchanger (20) is used as the counter electrode (32), and that streamer discharge is generated from the discharge electrode (31) towards the heat exchanger (20). As a result of such arrangement, there is no need to individually provide the counter electrode (32), and the number of component parts required in the air conditioner can be reduced. Besides, the air conditioner can be downsized and low-profiled by an amount corresponding to the space required for installation of the counter electrode (32) (if provided).

Additionally, in accordance with the ninth aspect of the present invention, air disturbance is caused in the vicinity of the heat exchanger (20) by an ion wind which is generated accompanied with the streamer discharge. That is, the efficiency of heat exchange of the heat exchanger (20) is improved by the stirring effect of air in the vicinity of the heat exchanger (20).

REFERENCE NUMERALS IN THE DRAWINGS

10: air conditioner
15: air passageway
20: heat exchanger
30: discharge unit (discharge means)
31: discharge electrode
32: counter electrode
40: catalytic unit (catalytic means)
41: prefilter (dust particle collecting means)

BEST EMBODIMENT MODE FOR CARRYING OUT THE INVENTION

Hereinafter, embodiments of the present invention will be described in detail with reference to the accompanying drawings.

An air conditioner (10) according to an embodiment of the present invention is a so-called wall type room air conditioner which is mounted on a room side wall. This air conditioner (10) performs air conditioning of room air as air to be treated, simultaneously with purification thereof.

Figure 1:
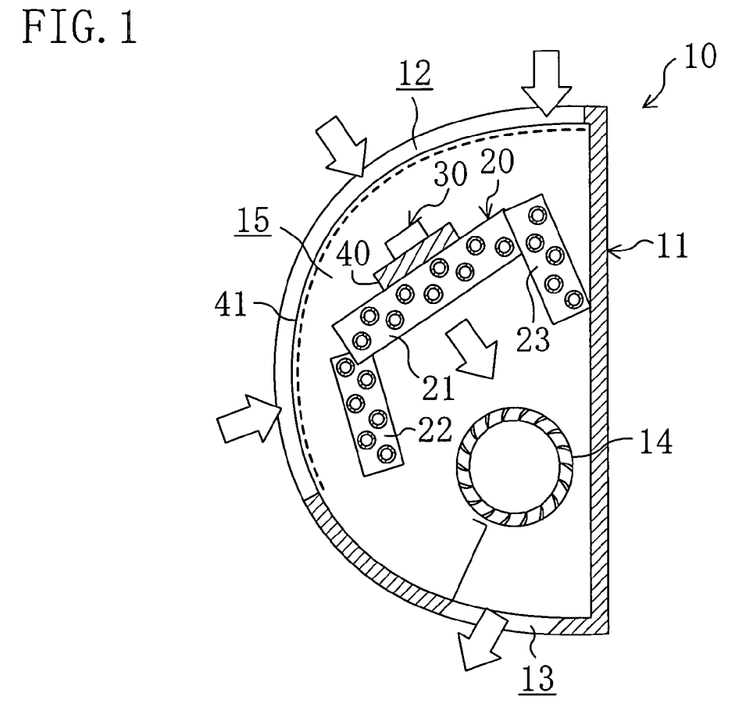
FIG. 1 is a vertical cross sectional view depicting the overall configuration of an air conditioner according to an embodiment of the present invention.

As shown in FIG. 1, the air conditioner (10) is provided with a horizontally-long, approximately semicylindrical casing (11). An inlet opening (12) and an outlet opening (13) are formed in the casing (11). The inlet opening (12) serves as an air introducing opening through which room air is taken into the casing (11). The inlet opening (12) is formed in an approximately upper half portion of the front surface (left-hand surface in FIG. 1) of the casing (11). On the other hand, the outlet opening (13) serves as an air supplying opening through which air which has been treated in the air conditioner (10) is supplied into an indoor space from within the casing (11).

Formed between the inlet opening (12) and the outlet opening (13) in the casing (11) is an air passageway (15) through which air to be treated flows. The air passageway (15) contains (in upstream to downstream order relative to the flow of air): a prefilter (41), a discharge unit (30), a catalytic unit (40), a heat exchanger (20), and a fan (14).

The prefilter (41) is mounted in the internal vicinity of the inlet opening (12) so as to extend therealong. The prefilter (41) is disposed over the entire area of the inlet opening (12). The prefilter (41) constitutes a dust particle collecting means for trapping dust particles present in the air to be treated.

Figure 2:
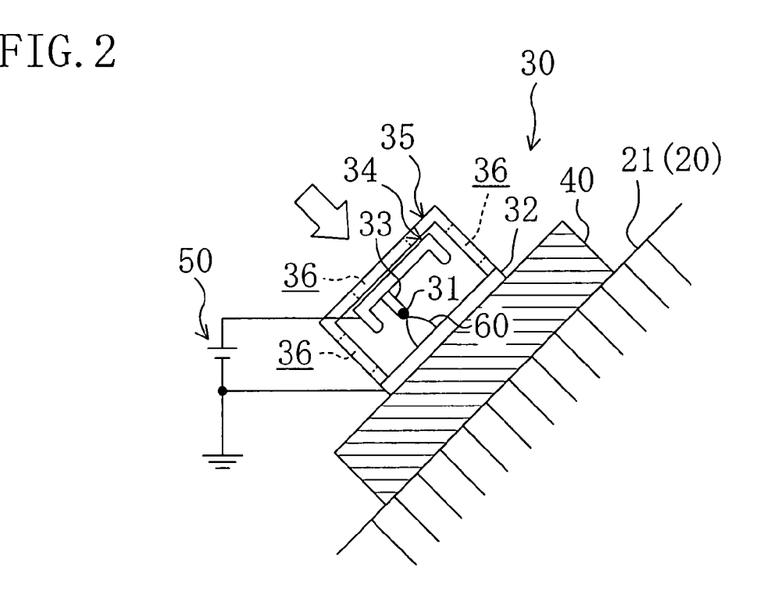
FIG. 2 is a schematic configuration diagram showing in enlarged manner a discharge unit of the air conditioner of the embodiment, when viewed from side.

The discharge unit (30) constitutes a discharge means which generates streamer discharge for decomposing the component to be processed present in the air to be treated. As shown in FIG. 2, the discharge unit (30) is provided with an insulating cover (35) and a discharge substrate (34).

The insulating cover (35) is formed by a lengthy member having a vertical cross section of squared U-shape. The insulating cover (35) is oriented such that its opened portion faces towards the downstream side of the flow of air. The insulating cover (35) is formed of such material as resin and glass having insulative properties. In addition, a plurality of air circulating holes (36) are formed through the wall surfaces of the insulating cover (35).

Figure 3:
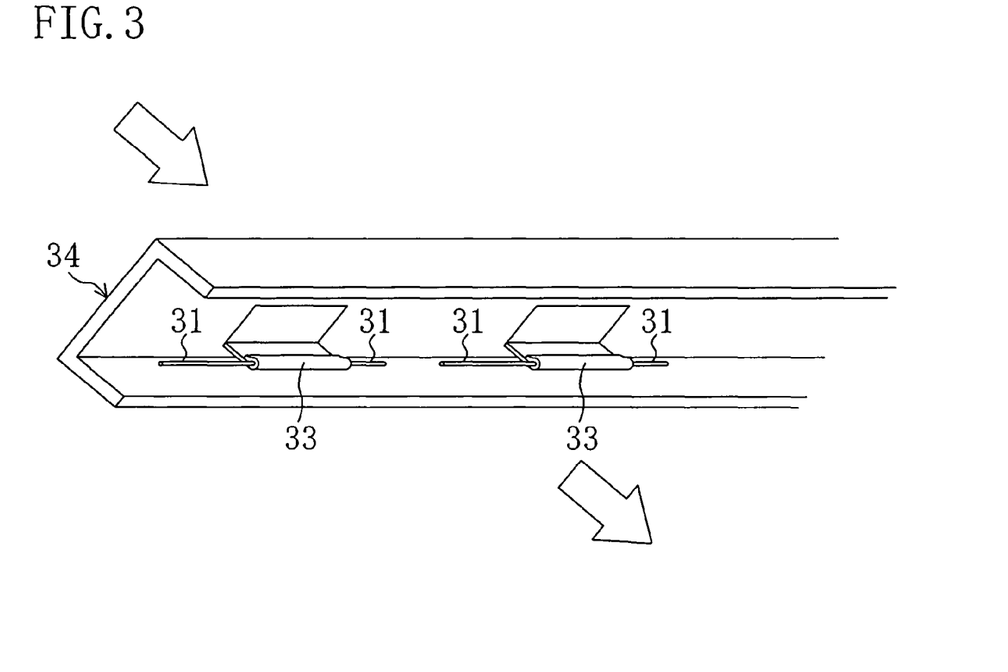
FIG. 3 is a perspective view of a discharge substrate of the air conditioner of the embodiment.

The discharge substrate (34) is disposed inside the insulating cover (35). Like the insulating cover (35), the discharge substrate (34) is formed by a lengthy member having a vertical cross section of squared U-shape. In addition, as shown in FIG. 3, a plurality of supporting plates (33) are formed inside the opened portion of the discharge substrate (34). The supporting plates (33) are formed by bending, in the direction of air flow, predetermined parts of a central plate (34a) of the discharge substrate (34). Each supporting plate (33) is, at its downstream end, is folded back in the opposite direction. In addition, each supporting plate (33) supports, at its folded-back part, its associated discharge electrode (31).

The discharge electrode (31) is formed in a linear shape or in a rod-like shape, and extends in a horizontal direction perpendicular to the flow of air. The discharge electrode (31) is formed of a tungsten wire having a wire diameter of about 0.2 mm. And the tip of the discharge electrode (31) constitutes a streamer discharge base end.

As shown in FIG. 2, the discharge unit (30) is provided with a counter electrode (32) facing towards the discharge electrode (31). The counter electrode (32) is formed in a plate-like shape or in a sheet-like shape. And the counter electrode (32) is disposed approximately in parallel with the discharge electrode (31). In the present embodiment, the distance between the discharge electrode (31) and the counter electrode (32) is 6.1 mm plus/minus 0.3 mm.

Referring to FIG. 2, the discharge unit (30) is provided with a high-voltage, direct-current power supply (50). The positive electrode side of the dc power supply (50) is electrically connected through the discharge substrate (34) to the discharge electrode (31). On the other hand, the negative electrode side (earth side) of the dc power supply (50) is electrically connected to the counter electrode (32).

In the discharge unit (30) having the above-described configuration, upon application of voltage to both the electrodes (31, 32), streamer discharge advances towards the counter electrode (32) from the tip of the discharge electrode (31). As a result, an active species (radical, fast electron, excited molecule et cetera) for decomposing the component to be processed is produced in the air.

The catalytic unit (40) is a substrate of honeycomb structure on which surface a plasma catalyst is supported. As the plasma catalyst, catalysts of the manganese family or so-called photocatalysts (titanium dioxide, zinc oxide, tungsten oxide, cadmium sulfide et cetera) may be used. The catalytic unit (40) constitutes a catalytic means which is activated by the active species generated by the streamer discharge in the discharge unit (30), thereby promoting decomposition of the component to be processed. In addition, an adsorbent for adsorbing the component to be processed is supported on the surface of the substrate of the catalytic unit (40). As the adsorbent, for example, zeolite, activated carbon and so on may be used.

The heat exchanger (20) is connected to an outdoor unit (not diagrammatically shown), and constitutes a part of a refrigerant circuit through which refrigerant is circulated to perform a refrigeration cycle. The heat exchanger (20) constitutes an air heat exchanger of the so-called fin and tube type. As shown in FIG. 1, three heat exchangers (21, 22, 23) are disposed in the air passageway (15). The first heat exchanger (21) is disposed in the obliquely posteroinferior vicinity of the discharge unit (30) and the catalytic unit (40). And, as shown in FIG. 2, the discharge electrode (31), the counter electrode (32), and the catalytic unit (40) are disposed such that they extend along an air inflow surface of the first heat exchanger (21). The second heat exchanger (22) is disposed near the front of the air passageway (15) and in the vicinity of the lower end of the inlet opening (12). The third heat exchanger (23) is disposed near the rear of the air passageway (15) and in the vicinity of the upper end of the inlet opening (12).

Running Operation

Next, description will be made in terms of the running operation of the air conditioner (10) of the present invention. Note that in the following description a cooling mode of operation of the air conditioner (10) is described by way of example.

As shown in FIG. 1, during operation of the air conditioner (10), the fan (14) enters the running state. In addition, direct-current voltage is applied to the discharge unit (30) from the dc power supply (50), and streamer discharge is performed in the discharge unit (30). Furthermore, low-pressure liquid refrigerant is circulated within the heat exchanger (20), wherein the heat exchanger (20) functions as an evaporator.

Upon introduction of room air into the casing (11) through the inlet opening (12), the air then passes through the prefilter (41). In the prefilter (41), dust particles present in the air are trapped. The air after dust particle removal by the prefilter (41) flows in the vicinity of the discharge unit (30) and the catalytic unit (40).

As shown in FIG. 2, in the discharge unit (30), a streamer discharge (60) advances from the tip of the discharge electrode (31) towards the counter electrode (32). And, in the vicinity of the discharge unit (30), the aforesaid active species is generated by the streamer discharge (60). Consequently, the component to be processed present in the air is oxidatively decomposed by the aforesaid active species. Furthermore, the active species activates the plasma catalyst of the catalytic unit (40). As a result, the component to be processed present in the air is further decomposed.

Even in the case where the component to be processed still remains in the air after reaction between the component to be processed and the active species, such a remaining component is adsorbed by the adsorbent of the catalytic unit (40). In addition, also in the case where a by-product is newly produced after reaction between the active species and the component to be processed, the resulting by-product is also adsorbed by the adsorbent of the catalytic unit (40).

The air which has been purified during passage through the prefilter (41), then through the discharge unit (30), and then through the catalytic unit (40) flows through the heat exchanger (20). In the heat exchanger (20), evaporation heat of the refrigerant is extracted from the air to be treated, whereby the air to be treated is cooled. The air which has been purified and conditioned in temperature in the way as described above is supplied through the outlet opening (13) into an indoor space to be air conditioned.

ADVANTAGEOUS EFFECTS OF THE EMBODIMENT

In the present embodiment, it is arranged such that the discharge unit (30) for performing streamer discharge is disposed in the air passageway (15) of the air conditioner (10). As a result of such arrangement, it becomes possible to produce active species in larger amounts when compared, for example, to glow discharge and corona discharge, whereby the capability of decomposing the component to be processed in the air conditioner (10) can be enhanced. As a result, while achieving downsizing of the discharge unit (30) and, furthermore, achieving downsizing/low-profiling of the air conditioner (10), stable air purification efficiency can be obtained.

In addition to the above, in the present embodiment, it is arranged such that the rod-like discharge electrode (31) lies perpendicular to the flow of air while it extends along the air inflow surface of the heat exchanger (20). As a result of such arrangement, it becomes possible to compactedly dispose the discharge electrode (31) in the air passageway (15), whereby further low-profiling of the air conditioner (10) is accomplished.

Additionally, in the aforesaid embodiment, it is arranged such that the streamer discharge (60) advances from the tip of the discharge electrode (31) towards the counter electrode (32). As a result of such arrangement, the density of electric field of the discharge region increases, thereby making it possible to increase the amount of generation of the active species. This therefore makes it possible to further improve the capability of decomposing the component to be processed in the air conditioner (10). Besides, the discharge electrode (31) and the counter electrode (32) are disposed approximately in parallel with each other. Consequently, even where the tip of the discharge electrode (31) is melted by prolonged discharge in the discharge unit (30) and, as a result, becomes "withdrawn", the distance between the discharge electrode (31) and the counter electrode (32) is maintained at constant interval. This therefore makes it possible to continue to generate stable streamer discharge over a long period of time in the discharge unit (30).

In addition, in the aforesaid embodiment, it is arranged such that the catalytic unit (40) is disposed between the discharge unit (30) and the heat exchanger (20). As a result of such arrangement, the catalytic unit (40) is activated by the active species, whereby the capability of decomposing the component to be processed is further enhanced. In addition, the adsorbent is supported in the catalyst unit (40), whereby the component (of low concentration) to be processed remaining in the air can be adsorbed on the adsorbent, in other words the remaining component is removed.

In addition, in the aforesaid embodiment, it is arranged such that the prefilter (41) is disposed upstream of the discharge unit (30). This arrangement therefore makes it possible to prevent adhesion of dust particles with respect to the discharge unit (30). This therefore enables the discharge unit (30) to perform stable streamer discharge over a long period of time. Besides, owing to provision of the prefilter (41), adhesion of dust particles with respect to the heat exchanger (20) is also prevented, whereby the rate of heat exchange between the heat exchanger (20) and the air to be treated is prevented from degradation.

Variations of the Embodiment

Next, description will be made in terms of exemplary variations of the air conditioner (10) of the aforesaid embodiment which differ in configuration of the discharge unit (30) from the aforesaid embodiment.

First Variation

In the discharge unit (30) of the first variation (FIG. 4), the discharge electrode (31) is shaped like a plate with one of its sides formed in a sawtooth shape. On the other hand, the counter electrode (32) is disposed in the air passageway (15) in such an orientation that it lies approximately in parallel with the discharge electrode (31). And, with the discharge electrode (31) and the counter electrode (32) being perpendicular to the flow of air, these electrodes (31, 32) extend along the air inflow surface of the heat exchanger (20) (not diagrammatically shown). And, upon application of voltage to both the electrodes (31, 32) from the dc power supply (50), the streamer discharge (60) advances from the tip of each of the teeth of the discharge electrode (31) towards the counter electrode (32).

Figure 4:
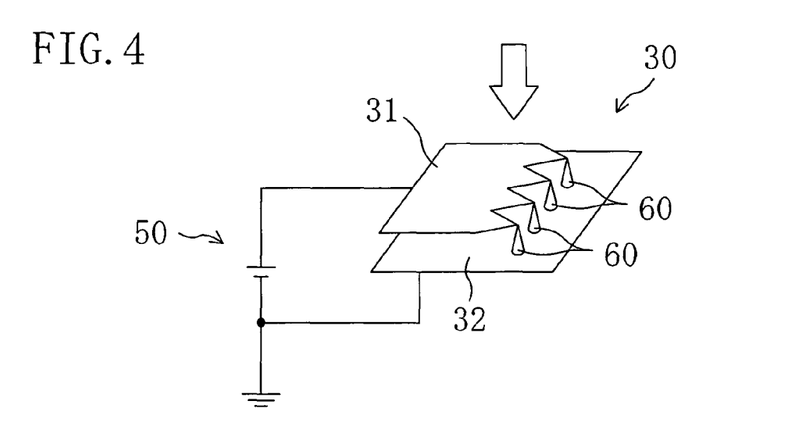
FIG. 4 is a schematic configuration diagram of a discharge unit according to a first variation of the embodiment.

Also in the first variation, the active species can be generated in large amounts by the streamer discharge (60), thereby making it possible to satisfactorily remove the component to be processed while achieving low-profiling of the discharge unit (30) and the air conditioner (10). In addition, the sawtooth-like discharge electrode (31) and the counter electrode (32) are disposed such that they lie perpendicular to the flow of air and extend along the air inflow surface of the heat exchanger (20), whereby the discharge unit (30) can be compactedly fitted in the air passageway (15) thereby accomplishing low-profiling of the air conditioner (10).

Second Variation

In the discharge unit (30) of the second variation (FIG. 5), the discharge electrode (31) shaped like a needle is supported on one side surface of the supporting plate (33) having a vertical cross section of L shape. This discharge electrode (31) is made up of a rod-like body part and a cone-like projected part formed at the tip of the body part. On the other hand, the counter electrode (32) is disposed in the air passageway (15) in such an orientation that it lies approximately in parallel with the discharge electrode (31). And, with the discharge electrode (31) and the counter electrode (32) being perpendicular to the flow of air, these electrodes (31, 32) extend along the air inflow surface of the heat exchanger (20) (not diagrammatically shown), as in the above-described embodiment. And upon application of voltage to both the electrodes (31, 32) from the dc power supply (50), the streamer discharge (60) advances from the projected part of the discharge electrode (31) towards the counter electrode (32).

Figure 5:
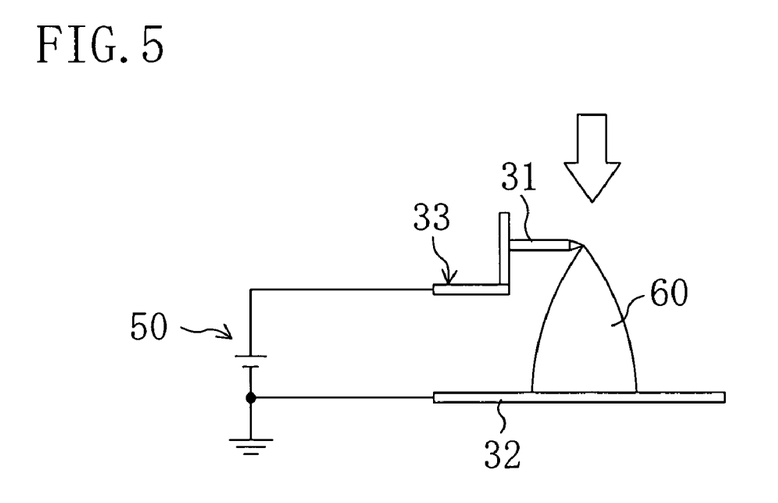
FIG. 5 is a schematic configuration diagram of a discharge unit according to a second variation of the embodiment.

Also in the second variation, the active species can be generated in large amounts by the streamer discharge (60), thereby making it possible to satisfactorily remove the component to be processed while achieving low-profiling of the air conditioner (10). In addition, the needle-like discharge electrode (31) and the counter electrode (32) are disposed such that they lie perpendicular to the flow of air and extend along the air inflow surface of the heat exchanger (20), whereby the discharge unit (30) can be compactedly fitted in the air passageway (15) thereby accomplishing low-profiling of the air conditioner (10).

Third Variation

Like the aforesaid embodiment, the discharge unit (30) of the third variation (FIG. 6) has an insulating cover (35), a discharge substrate (34), and a rod-like discharge electrode (31). On the other hand, the third variation differs from the aforesaid embodiment in that the plate-like counter electrode (32) is not provided, and that the tip of the discharge electrode (31) faces towards the heat exchanger (20). The heat exchanger (20) is formed mainly of electrically conductive aluminum and is electrically connected to the negative electrode side (earth side) of the dc power supply (50). And the heat exchanger (20) is configured such that it serves also as the counter electrode (32) of the aforesaid embodiment. More specifically, upon application of voltage to the discharge electrode (31) and the heat exchanger (20) from the dc power supply (50), the streamer discharge (60) advances from the tip of the rod-like discharge electrode (31) towards the surface of the heat exchanger (20). Although diagrammatical representation of the catalytic unit (40) is omitted in FIG. 6, the catalytic unit (40) may be disposed so as to allow streamer discharge between the discharge electrode (31) and the heat exchanger (20).

Figure 6:
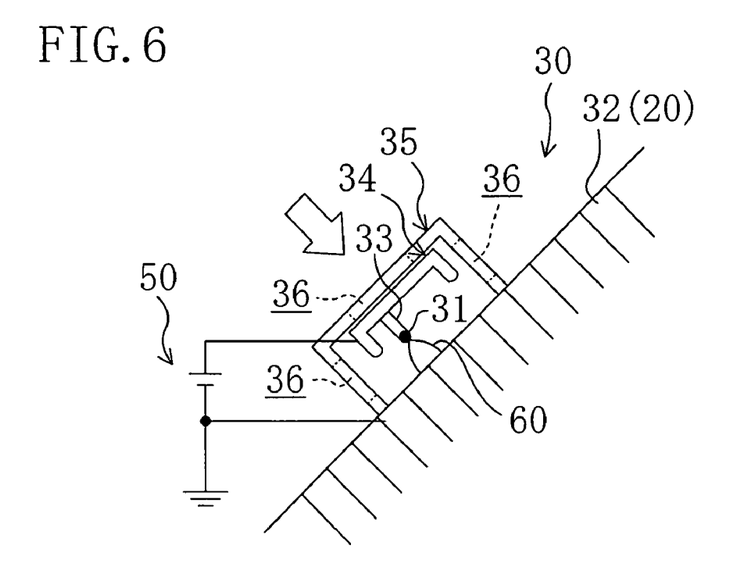
FIG. 6 is a schematic configuration diagram showing in enlarged manner a discharge unit according to a third variation of the embodiment, when viewed from side.

Also in the third variation, the active species can be generated in large amounts by the streamer discharge (60), thereby making it possible to satisfactorily remove the component to be processed while achieving low-profiling of the discharge unit (30) and the air conditioner (10).

In addition, in the third variation, the heat exchanger (20) is utilized as the counter electrode (32), wherein streamer discharge is generated from the discharge electrode (31) towards the heat exchanger (20). Consequently, there is no need to individually provide the counter electrode (32), thereby making it possible to reduce the number of component parts required in the air conditioner (10). Besides, the air conditioner (10) can be downsized and low-profiled by an amount corresponding to the space required for installation of the counter electrode (32) (if provided).

Furthermore, in the third variation, air disturbance is caused in the vicinity of the heat exchanger (20) by an ion wind which is generated accompanied with the streamer discharge. That is, the efficiency of heat exchange of the heat exchanger (20) is improved by the stirring effect of air in the vicinity of the heat exchanger (20).

Another Embodiment

The aforesaid embodiment may be configured as follows.

In the aforesaid embodiment, the prefilter (41) is provided as a trapping means for trapping airborne dust particles. Alternatively, an electrical dust particle collector or other like dust particle collectors may be disposed as a substitute for the prefilter (41).

In addition, in the aforesaid embodiment, the heat exchanger (20) configured to perform only temperature conditioning of the air to be treated is provided as an air conditioning means. Alternatively, as an air conditioning means other than the heat exchanger (20), an adsorbent for adsorption and desorption of airborne moisture, a humidifier for air humidification, or some like means may be provided.

It should be noted that the above-descried embodiments are essentially preferable examples which are not intended in any sense to limit the scope of the present invention, its application, or its range of application.

INDUSTRIAL APPLICABILITY

As has been described above, the present invention finds utility in the field of air conditioners capable of purification of air to be treated.

What is claimed is:

1. An air conditioner, comprising:
an air passageway through which air to be treated flows; and
an air conditioning unit providing air conditioning to air flowing through the air passageway,
wherein the air passageway is provided with a discharge unit configured to perform streamer discharge,
the discharge unit includes a discharge electrode serving as a discharge base end and a counter electrode serving as a discharge terminal end,
the discharge electrode has a rod shape or a linear shape and extends in a direction perpendicular to a flow of air,
the counter electrode has a plate shape and is disposed approximately in parallel with the discharge electrode, and
the discharge unit is configured to perform streamer discharge from a tip of the discharge electrode towards the counter electrode.

2. The air conditioner of claim 1,
wherein the discharge electrode is formed so as to extend, along the air conditioning unit, in a direction perpendicular to the flow of air.

3. The air conditioner of claim 1 or 2,
wherein voltage is applied to the discharge unit from a high-voltage direct-current power supply.

4. The air conditioner of claim 1 or 2,
wherein a catalytic unit configured to be activated by an active species generated by streamer discharge from the discharge unit to thereby promote decomposition of a component to be processed, is disposed downstream of the discharge unit.

5. The air conditioner of claim 4,
wherein the discharge unit and the catalytic unit are disposed upstream of the air conditioning unit.

6. The air conditioner of claim 4,
wherein the catalytic unit supports thereon an adsorbent for adsorption of the component to be processed present in the air.

7. The air conditioner of claim 1,
wherein the air passageway is provided with dust particle collecting unit trapping dust particles present in the air.

8. The air conditioner of claim 7,
wherein the dust particle collecting unit is disposed upstream of the discharge unit.

9. The air conditioner of claim 2,
wherein the air conditioning unit is formed by a conductive heat exchanger which is disposed so as to face towards the discharge electrode, and
wherein the heat exchanger serves also as the counter electrode.

10. The air conditioner of claim 5,
wherein the catalytic unit supports thereon an adsorbent for adsorption of the component to be processed present in the air.

* * * * *